US010506765B2

(12) United States Patent
Zhu

(10) Patent No.: US 10,506,765 B2
(45) Date of Patent: Dec. 17, 2019

(54) INTELLIGENT LIGHT ADJUSTING SYSTEM AND INTELLIGENT LIGHT ADJUSTING METHOD IN CROP GROWTH PROCESS

(71) Applicant: BOE TECHNOLOGY GROUP CO., LTD., Beijing (CN)

(72) Inventor: Lin Zhu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 494 days.

(21) Appl. No.: 15/300,970

(22) PCT Filed: Jan. 18, 2016

(86) PCT No.: PCT/CN2016/071169
§ 371 (c)(1),
(2) Date: Sep. 30, 2016

(87) PCT Pub. No.: WO2017/020560
PCT Pub. Date: Feb. 9, 2017

(65) Prior Publication Data
US 2017/0181384 A1 Jun. 29, 2017

(30) Foreign Application Priority Data
Aug. 3, 2015 (CN) .......................... 2015 1 0479313

(51) Int. Cl.
*G01N 21/64* (2006.01)
*A01G 7/04* (2006.01)
(Continued)

(52) U.S. Cl.
CPC ............. *A01G 7/045* (2013.01); *A01G 22/00* (2018.02); *G01J 1/44* (2013.01); *G01N 21/64* (2013.01)

(58) Field of Classification Search
CPC .... A01G 7/045; G01J 1/42; G01J 2001/4247; G01N 2021/635; G01N 2021/8466; G01N 21/64; G01N 21/6486; Y02P 60/146
See application file for complete search history.

(56) References Cited

U.S. PATENT DOCUMENTS 5,014,225 A * 5/1991 Vidaver ................. G01N 21/64
250/461.2
2005/0072935 A1 4/2005 Lussier
(Continued)

FOREIGN PATENT DOCUMENTS

CN 101636076 A 1/2010
CN 104488582 A 4/2015
(Continued)

OTHER PUBLICATIONS

Second Office Action for Chinese Application No. 201510479313.4, dated Aug. 23, 2017, 6 Pages.
(Continued)

*Primary Examiner* — Marcus H Taningco
(74) *Attorney, Agent, or Firm* — Brooks Kushman P.C.

(57) ABSTRACT

An intelligent light adjusting system and method thereof in a crop growth process are provided. The intelligent light adjusting system includes a parameter measurement device, a parameter processing device, a light source control device and a light source assembly. The parameter measurement device is for measuring a specified parameter in the crop growth process. The parameter processing device is for acquiring a light source parameter of the light source control device, based on the specified parameter. The light source control device is for controlling lighting of the light source assembly, based on the light source parameter.

12 Claims, 3 Drawing Sheets

(51) Int. Cl.
*A01G 22/00* (2018.01)
*G01J 1/44* (2006.01)

(56) References Cited

U.S. PATENT DOCUMENTS

| | | | |
|---|---|---|---|
| 2010/0115830 A1* | 5/2010 | Dube | A01G 7/045 47/17 |
| 2013/0040380 A1 | 2/2013 | Hunt et al. | |
| 2017/0265408 A1* | 9/2017 | McGowan | A01G 22/00 |
| 2017/0339839 A1* | 11/2017 | Carstensen | A01G 7/045 |

FOREIGN PATENT DOCUMENTS

| | | |
|---|---|---|
| CN | 104703464 A | 6/2015 |
| CN | 104982242 A | 10/2015 |
| WO | 2008068699 A1 | 6/2008 |

OTHER PUBLICATIONS

Chinese First Office Action for Chinese Application No. 201510479313.4, dated Dec. 27, 2016, 7 Pages.

International Search Report and Written Opinion for Application No. PCT/CN2016/071169, dated Jan. 18, 2016, 15 Pages.

\* cited by examiner

INTELLIGENT LIGHT ADJUSTING SYSTEM AND INTELLIGENT LIGHT ADJUSTING METHOD IN CROP GROWTH PROCESS

CROSS-REFERENCE TO RELATED APPLICATIONS

This application is the U.S. national phase of PCT Application No. PCT/CN2016/071169 filed on Jan. 18, 2016, which claims priority to Chinese Patent Application No. 201510479313.4, filed on Aug. 3, 2015, the disclosures of which are incorporated in their entirety by reference herein.

TECHNICAL FIELD

The disclosure relates to the field of agricultural production, and in particular, to an intelligent light adjusting system and an intelligent light adjusting method in a crop growth process.

BACKGROUND

With the development of intelligent agricultural production, artificial light instead of natural light is used to cultivate crops in the agricultural field. In a relevant automatic supplemental lighting system, generally, supplemental lighting is performed by using outside light intensity as a standard. This supplemental lighting method has advantages of simple design, easy parameter adjustment, but the growth state of crops cannot be analyzed based on internal factors of the crops.

SUMMARY

An intelligent light adjusting system and method thereof in a crop growth process are provided according to embodiments of the disclosure. Technical solutions are provided as follows.

In a first aspect, an intelligent light adjusting system in a crop growth process is provided. The intelligent light adjusting system includes: a parameter measurement device, a parameter processing device, a light source control device and a light source assembly. The parameter measurement device is for measuring a specified parameter in the crop growth process; the parameter processing device is for acquiring a light source parameter of the light source control device, based on the specified parameter; and the light source control device is for controlling the lighting of the light source assembly, based on the light source parameter.

Optionally, the specified parameter may be a chlorophyll fluorescence parameter.

Optionally, the parameter measurement device may include: a photosensitive element, a sensor element, a signal conditioning and converting circuit and an auxiliary circuit. The photosensitive element is for sensing light, converting the sensed light into a valid optical signal and transmitting the valid optical signal to the sensor element; the sensing element is for converting the valid optical signal into an electrical signal and transmitting the electrical signal to the signal conditioning and converting circuit; the signal conditioning and converting circuit is for amplifying a valid signal in the electrical signal and filtering out an invalid noise signal from the electrical signal to obtain a valid electrical signal, and transmitting the valid electrical signal to the parameter processing device; and the auxiliary circuit is for comparing an output of the sensor element and an output of the signal conditioning and converting circuit and giving feedback, where the valid optical signal corresponds to the specified parameter.

Optionally, the parameter measurement device may include: test light sources, a reflective cup, a photoelectric detector and a signal amplifier. The test light sources are for providing lights for crops; the reflective cup is for converging the lights of the test light sources to improve light utilization efficiency; the photoelectric detector is for detecting the lights converged by the reflective cup, converting an optical signal obtained through detection into an electrical signal, and transmitting the electrical signal to the signal amplifier; and the signal amplifier is for amplifying the electrical signal and filtering out an invalid noise signal from the electrical signal to obtain a valid electrical signal.

Optionally, the test light sources may include light sources providing measuring radiation, actinic radiation, saturation radiation, and far-red radiation respectively, and a long wavelength cut-off filter is arranged between the light source providing measuring radiation and the reflective cup.

Optionally, the reflective cup is arranged above leaves for testing of the crops, and a short wavelength cut-off filter is arranged between the leaves for testing of the crops and the photoelectric detector.

Optionally, the light source control device may include: a micro control unit for receiving the light source parameter outputted by the parameter processing device, and controlling a pulse width modulation unit based on the light source parameter; and the pulse width modulation unit for outputting a current to adjust luminance of the light source assembly, based on the control of the micro control unit.

Optionally, the light source assembly may include multiple light emitting diodes (LEDs), the light source control device further includes an LED driver circuit, and the pulse width modulation unit is for adjusting the luminance of the light source assembly by means of the LED driver circuit.

Optionally, the parameter measurement device is for transmitting the specified parameter to the parameter processing device, in a case that the specified parameter measured currently is greater than a first preset threshold; and the parameter measurement device is for transmitting the specified parameter to the parameter processing device, in a case that the specified parameter measured currently is less than a second preset threshold, where the first preset threshold is greater than the second preset threshold.

Optionally, the parameter processing device is for outputting a first light source parameter to reduce luminance of the light source assembly, in a case that the specified parameter measured currently is greater than a third preset threshold; or the parameter processing device is for outputting a second light source parameter to increase the luminance of the light source assembly, in a case that the specified parameter measured currently is less than a fourth preset threshold, where the third preset threshold is greater than the fourth preset threshold.

Optionally, the light source assembly includes multiple LEDs.

In a second aspect, an intelligent light adjusting method in a crop growth process is provided, which includes: measuring a specified parameter in the crop growth process; and adjusting, based on the specified parameter, a light source parameter of the light source assembly to adjust light for crops.

Optionally, luminance of the light source assembly is reduced, in a case that the specified parameter measured currently is greater than a third preset threshold; or the luminance of the light source assembly is increased, in a case that the specified parameter measured currently is less than a fourth preset threshold, where the third preset threshold is greater than the fourth preset threshold.

In the technical solutions according to the embodiments of the present disclosure, the photosynthetic efficiency of the crops can be reflected by using a certain specified parameter during the growth of the crops as an adjusting reference, and a lighting condition is adjusted based on the growth situation of the crops, thereby improving the accuracy and efficiency in adjusting light, and facilitating the growth of the crops.

BRIEF DESCRIPTION OF THE DRAWINGS

The drawings to be used in the description of the embodiments are described briefly as follows, such that the technical solutions according to the embodiments of the present disclosure become clearer. It is apparent that the drawings in the following description only illustrate some embodiments of the present disclosure. For those skilled in the art, other drawings may be obtained based on these drawings without any creative work.

DETAILED DESCRIPTION

To make the technical solutions and advantages of the present disclosure clearer, embodiments of the present disclosure are described in detail with reference to drawings hereinafter.

Figure 1:
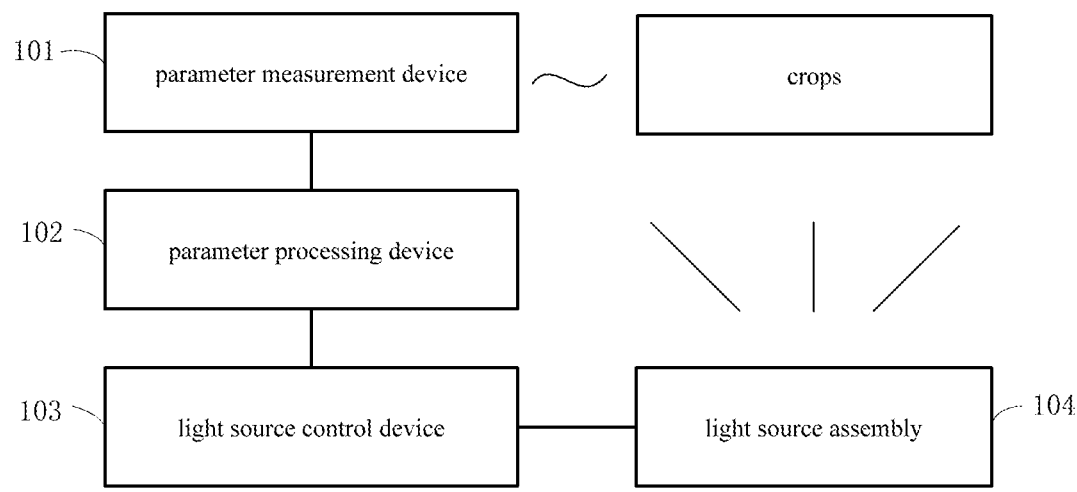
FIG. 1 is a schematic structural diagram of an intelligent light adjusting system in a crop growth process according to an embodiment of the disclosure.

FIG. 1 is a schematic structural diagram of an intelligent light adjusting system in a crop growth process according to an embodiment of the disclosure. Referring to FIG. 1, the intelligent light adjusting system includes: a parameter measurement device 101, a parameter processing device 102, a light source control device 103 and a light source assembly 104. The components in the intelligent light adjusting system are described below.

The parameter measurement device 101 is for measuring a specified parameter in the crop growth process. The specified parameter may be a chlorophyll fluorescence parameter.

The parameter measurement device 101 may be arranged in the growth environment of crops. For example, the parameter measurement device may be arranged in a cultivation greenhouse. Optionally, the parameter measurement device 101 is for transmitting the specified parameter to the parameter processing device 102, in a case that the specified parameter measured currently is greater than a first preset threshold. It should be noted that, the light adjustment process of the intelligent light adjusting system may be triggered under some conditions. For example, in a case that the specified parameter is greater than the first preset threshold, it indicates that the crops suffer from excessive light, and the light needs to be reduced. In this case, the parameter measurement device 101 needs to transmit the specified parameter to the parameter processing device 102, such that the parameter processing device 102 adjusts light based on the specified parameter.

The parameter measurement device 101 is further for transmitting the specified parameter to the parameter processing device 102, in a case that the specified parameter measured currently is less than a second preset threshold, where the first preset threshold is greater than the second preset threshold. It should be noted that, the light adjustment process of the intelligent light adjusting system may be triggered under some conditions. For example, in a case that the specified parameter is greater than the second preset threshold and less than the first preset threshold, it indicates that the crops get sufficient light and the current light source may not be adjusted. In this case, the parameter measurement device 101 has no need to transmit the specified parameter to the parameter processing device 102. In a case that the specified parameter is less than or equal to the second preset threshold, it indicates that the crops get insufficient light, and light needs to be supplemented. In this case, the parameter measurement device 101 needs to transmit the specified parameter to the parameter processing device 102, such that the parameter processing device 102 adjusts light based on the specified parameter.

Figure 2:
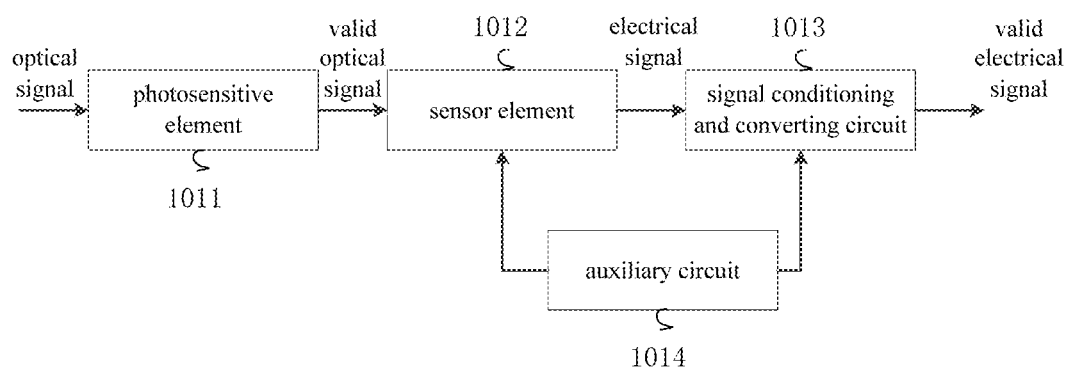
FIG. 2 is a schematic structural diagram of a parameter measurement device according to an embodiment of the disclosure.

Referring to FIG. 2, a structure of the parameter measurement device 101 according to an embodiment includes: a photosensitive element 1011, a sensor element 1012, a signal conditioning and converting circuit 1013 and an auxiliary circuit 1014.

The operating principles of the above-mentioned elements in the parameter measurement device 101 are described as follows. The photosensitive element 1011 is for sensing light, converting the sensed light into a valid optical signal and transmitting the valid optical signal to the sensor element 1012. In an embodiment of the disclosure, the photosensitive element 1011 may detect the content of fluorescence substance generated due to photochemical reactions during the process of photosynthesis in a space to be tested. The photosensitive element 1011 converts an optical signal into the valid optical signal, and the valid optical signal corresponds to the content of the fluorescence substance.

The sensor element 1012 is for converting the valid optical signal into an electrical signal and transmitting the electrical signal to the signal conditioning and converting circuit 1013.

The signal conditioning and converting circuit 1013 is for amplifying a valid signal in the electrical signal and filtering out an invalid noise signal from the electrical signal to obtain a valid electrical signal, and transmitting the valid electrical signal to the parameter processing device to perform subsequent light control.

The auxiliary circuit 1014 may compare an output of the sensor element 1012 and an output of the signal conditioning and converting circuit 1013 and give feedback, to improve the accuracy of the whole detection and ensure the reliability and stability of the system.

Figure 3:
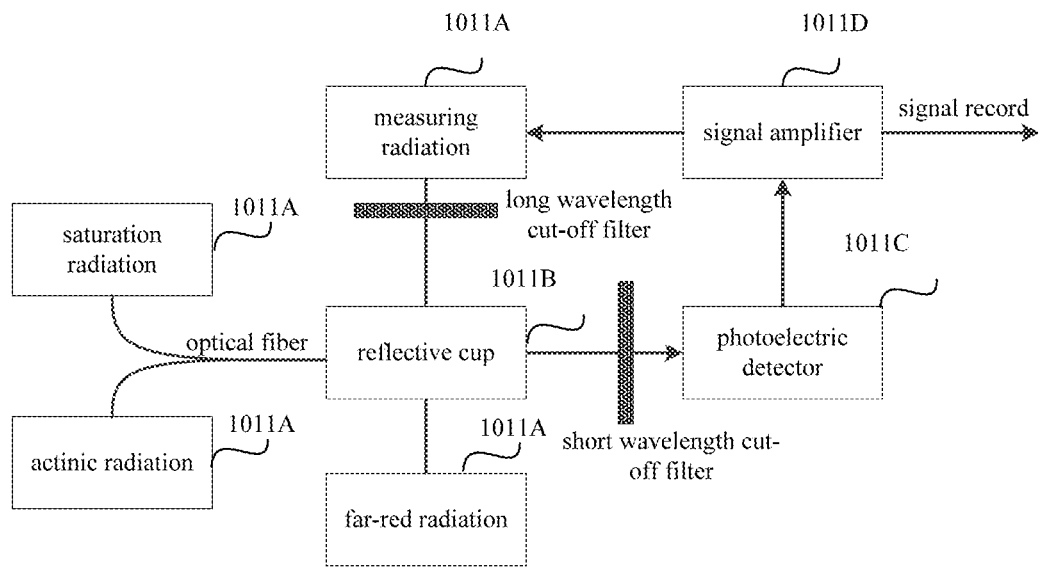
FIG. 3 is a schematic structural diagram of a photosensitive element according to an embodiment of the disclosure.

Referring to FIG. 3, a structure of the parameter measurement device 101 according to an embodiment includes: test light sources 1011A, a reflective cup 1011B, a photoelectric detector 1011C and a signal amplifier 1011D. The test light source 1011A is for providing light for the crop. The reflective cup 1011B is for converging lights of the test light sources to improve light utilization efficiency. The photoelectric detector 1011C is for detecting a valid optical signal obtained through converging by the reflective cup and filtering out an invalid optical signal, converting the detected valid optical signal into an electrical signal, and transmitting the electrical signal to the signal amplifier 1011D. The signal amplifier 1011D is for amplifying the electrical signal to obtain a valid electrical signal.

The reflective cup 1011B is arranged above leaves of the crops selected as test samples. As shown in FIG. 3, the reflective cup 1011B may be connected to the test light sources through light fibers. The lights from the test light sources are converged by the reflective cup 1011B and then fall on the test samples below the reflective cup 1011B.

The test light sources 1011A include light sources providing measuring radiation, actinic radiation, saturation radiation, and far red radiation. The reflective cup 1011B may be connected to the light sources providing actinic radiation and the saturation radiation through light fibers.

Measuring radiation (MR) is weak red radiation generated by a light emitting diode, and its photon flux density (abbreviated as PFD, indicating the light irradiation amount per unit time per unit area) is less than 0.2 $\mu mol \cdot m^{-2} \cdot s^{-1}$, with a wavelength of 650 nm. Generally, a long wavelength cut-off filter ($\lambda$<670 nm, that is, the long wavelength cut-off filter is used to ensure that the light falling on the leaves of crops is measuring radiation with a wavelength less than 670 nm) is arranged between the light emitting diode and the reflective cup 1011B. After energy of the measuring radiation is absorbed by the test samples, a part of excitation radiation is emitted in the form of fluorescence, and is detected by the photoelectric detector 1011C. A short wavelength cut-off filter ($\lambda$>700 nm, that is, the short wavelength cut-off filter is used to cut off measuring radiation with a wavelength greater than 700 nm) and a heat absorbing filter (which is used to filter out the measuring radiation and only enable a fluorescence signal to pass) are arranged between the leaves of the crops to be tested and the photoelectric detector 1011C.

Actinic Radiation (AR) is red radiation with a wavelength of 665 nm generated by a serial of light emitting diodes, and its PFD is generally a few hundred $\mu mol \cdot m^{-2} \cdot s^{-1}$. A highly selective amplification system is used to avoid interference of a non-fluorescent signal, and the highly selective amplification system with high accuracy leads to more reliable test results. After energy of the actinic radiation is absorbed by the test samples, a part of the excitation radiation may be reflected by the test samples or may transmit through the test samples, and the reflected radiation can be filtered out by the short wavelength cut-off filter.

A saturation radiation (SR) light source may be a halogen lamp which can emit strong white radiation (its PFD can be up to 10000 $\mu mol \cdot m^{-2} \cdot s^{-1}$). After SR is added, any photochemical processes does not occur (that is, a chemical reaction equilibrium constant kp equals 0), and all the absorbed energy is converted into heat and fluorescence. In case of adding SR, generally the frequency of MR is increased, in order to obtain a high signal to noise ratio. The role of the SR is to maintain a fluorescent product of photosynthesis, such that the fluorescent product is not quickly quenched.

Far-red radiation (FR) is far-red radiation with a wavelength of 735 nm, which induces reduction reaction in photosynthesis to rapidly occur to ensure the measurement process of photosynthesis, such that the fluorescent product, i.e., the valid optical signal, can be detected by the photoelectric detector.

The parameter processing device 102 is for acquiring a light source parameter of the light source control device 103, based on the specified parameter.

Optionally, the parameter processing device 102 is used to output a first light source parameter to reduce luminance of the light source assembly, in a case that the specified parameter measured currently is greater than a third preset threshold; or the parameter processing device is used to output a second light source parameter to increase the luminance of the light source assembly, in a case that the specified parameter measured currently is less than a fourth preset threshold, where the third preset threshold is greater than the fourth preset threshold.

It should be noted that the parameter processing device 102 may acquire a source parameter corresponding to the current specified parameter according to a preset correspondence between the specified parameter and the light source parameter stored in a parameter setting database. As illustrated in the description about the parameter measurement device 101, the value of the specified parameter may be used to trigger the adjustment for the light source parameter to increase or decrease the luminance of the light source assembly to vary the light intensity for the crops, thereby providing flexible and efficient lighting for the crops according to the actual photosynthesis situation of the crops.

The light source control device 103 is for controlling the lighting of the light source assembly 104, based on the light source parameter.

Figure 4:
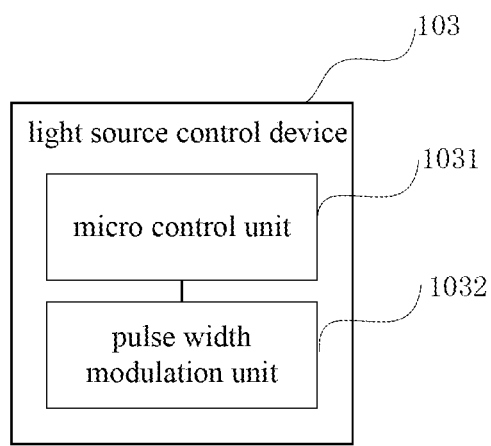
FIG. 4 is a schematic structural diagram of a light source control device according to an embodiment of the disclosure.

Referring to FIG. 4, the light source control device 103 includes a micro control unit 1031 and a pulse width modulation unit 1032.

The micro control unit 1031 is for receiving the light source parameter outputted by the parameter processing device 102, and controlling the pulse width modulation unit 1032 based on the light source parameter. The micro control unit 1031 may be a single chip microcomputer, an ARM or the like, and process the obtained light source parameter to control and adjust the light of LED.

The pulse width modulation unit 1032 is for outputting a current to adjust luminance of the light source assembly, based on the control of the micro control unit. In an embodiment of the present disclosure, various modes of pulse width modulation (PWM) may be used to control the luminance of the light emitting diode (LED). The pulse width modulation process can be achieved by controlling the duty cycle.

Figure 5:
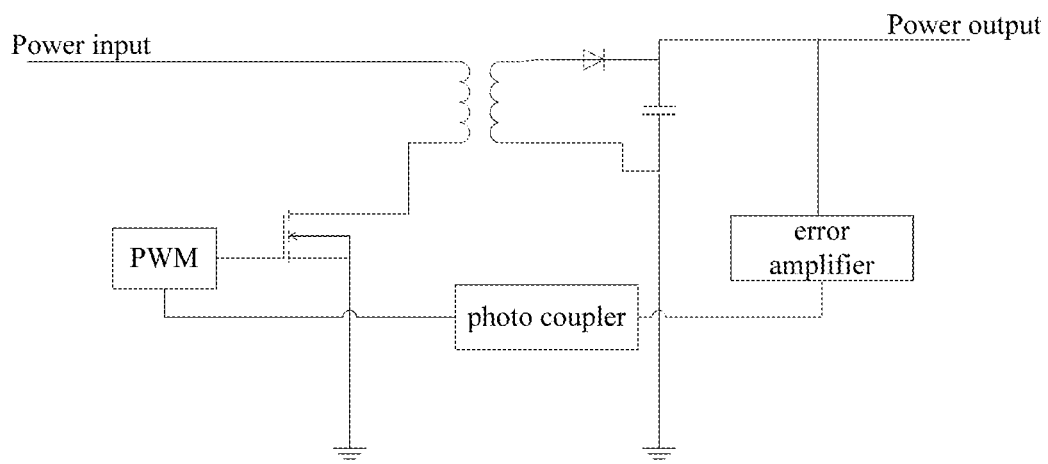
FIG. 5 is a schematic structural diagram of a pulse width modulation unit and a drive circuit according to an embodiment of the disclosure.

Furthermore, the light source control device 103 may further include a LED driver circuit 1033. The pulse width modulation unit 1032 can regulate the light source assembly 104 by means of the LED driver circuit 1033. The LED driver circuit 1033 may have a structure as shown in FIG. 5. The LED driver circuit 1033 has a main function to supply power for the LED using PWM control. Here, a flyback topology is used, which has a high efficiency, good stability, and an isolation effect, thereby ensuring the accuracy adjustment as well as reliability and stability of power supply. Specifically, the driver circuit 1033 may include a MOSFET, an error amplifier and a photo coupler. The operating principle thereof is as follows. A signal outputted by pulse width modulation unit 1032 is applied to the MOSFET to control the MOSFET to be turned on or turned off, power at an input terminal is transferred to an output terminal through a transformer, and power transfer control varies with the adjustment on duty cycle. In this way, an outputted current can be controlled, thereby controlling the luminance of the LED.

Optionally, the light source assembly 104 includes multiple LEDs.

Optionally, the above parameter processing device and light source control device have the functions as follows. A specified parameter M1 obtained by measuring the crops in the photosynthetic reaction period is compared with the specified parameter M0 obtained in the above sampling process. In a case that M1 is greater than or equal to M0, the current may be controlled to be reduced by a value to maintain photosynthesis without wasting energy. In a case that M1 is less than M0, it shows that the photosynthesis is insufficient, it needs to control the current to be increased by a value to stimulate sufficient photosynthesis, thereby increasing the specified parameter.

Based on the above-described specific structure of the intelligent light adjusting system, the 0-100% luminance of the LED may be achieved by adjusting the current flowing through the LED in the light source assembly, with adjustment accuracy of ±0.5%. With such high-precision current adjustment, the lighting may be controlled more precisely, chlorophyll fluorescence parameters do not fluctuate greatly, and the stability of control is better ensured.

Figure 6:
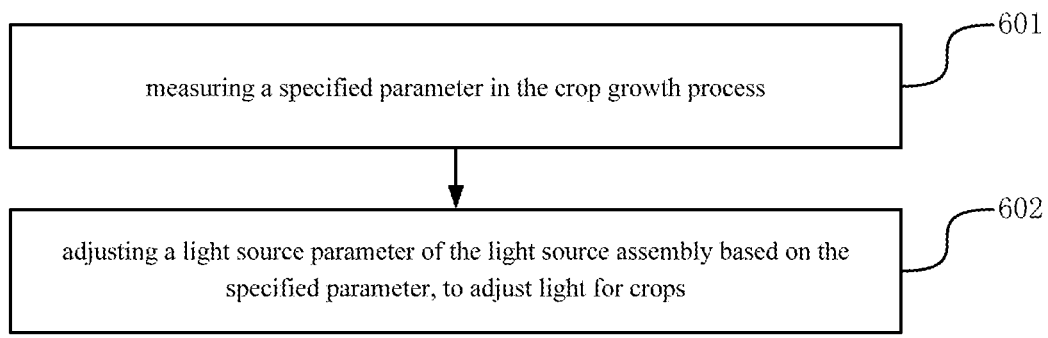
FIG. 6 is a flowchart of an intelligent light adjusting method in a crop growth process according to an embodiment of the disclosure.

In another aspect, an intelligent light adjusting method in a crop growth process is provided according to an embodiment of the disclosure. As shown in FIG. 6, the method includes steps 601 and 602.

In step 601, a specified parameter in the crop growth process is measured.

In step 602, a light source parameter of a light source assembly is adjusted based on the specified parameter, to adjust light for crops.

Optionally, the luminance of the light source assembly is reduced, in a case that the specified parameter measured currently is greater than a third preset threshold; or the luminance of the light source assembly is increased, in a case that the specified parameter measured currently is less than a fourth preset threshold, where the third preset threshold is greater than the fourth preset threshold.

The specific light adjusting process may be performed based on the intelligent light adjusting system according to the above embodiments, the specific implementation principle thereof is the same as that of the above intelligent light adjusting system, which is not repeated here.

All of the above optional technical solutions may be combined in any way to form optional embodiments of the present disclosure, which are not repeated here.

It should be noted that, the intelligent light adjusting method in the crop growth process according to the above-described embodiment is applied to the above-described intelligent light adjusting system, and the implementation process of the method is based on the same conception as the system embodiment. Concerning the implementation process of the method, reference can be made to the system embodiment, which is not repeated here.

It should be appreciated by those ordinary skilled in the art that all or part of the steps for achieving the above-described embodiments may be implemented by hardware, or by a program instructing relevant hardware. The program may be stored in a computer readable storage medium, which may be a read only memory, a magnetic disk or an optical disk.

The foregoing descriptions are only preferred embodiments of the present disclosure, which are not intended to limit the disclosure. Any modification, equivalents and improvements within the spirit and principles of the disclosure shall fall into the scope of protection of the disclosure.

What is claimed is:

1. An intelligent light adjusting system useable in a crop growth process, the intelligent light adjusting system comprising: a parameter measurement device, a parameter processing device, a light source control device and a light source assembly, wherein the parameter measurement device is configured to measure a specified parameter in the crop growth process;

the parameter processing device is configured to acquire a light source parameter of the light source control device, based on the specified parameter; and the light source control device is configured to control lighting of the light source assembly, based on the light source parameter, wherein the parameter measurement device comprises: a photosensitive element, a sensor element, a signal conditioning and converting circuit and an auxiliary circuit, wherein the photosensitive element is configured to sense light, convert the sensed light into a valid optical signal and transmit the valid optical signal to the sensor element;

the sensing element is configured to convert the valid optical signal into an electrical signal and transmit the electrical signal to the signal conditioning and converting circuit;

the signal conditioning and converting circuit is configured to amplify a valid signal in the electrical signal and filtering out an invalid noise signal from the electrical signal to obtain a valid electrical signal, and transmit the valid electrical signal to the parameter processing device; and the auxiliary circuit is configured to compare an output of the sensor element and an output of the signal conditioning and converting circuit and give feedback, wherein the valid optical signal corresponds to the specified parameter.

2. The intelligent light adjusting system according to claim 1, wherein the specified parameter is a chlorophyll fluorescence parameter.

3. The intelligent light adjusting system according to claim 1, wherein the parameter measurement device comprises: test light sources, a reflective cup, a photoelectric detector and a signal amplifier, wherein the test light sources are configured to provide lights for crops;

the reflective cup is configured to converge the lights of the test light sources to improve light utilization efficiency;

the photoelectric detector is configured to detect the lights converged by the reflective cup, convert an optical signal obtained through detection into an electrical signal, and transmit the electrical signal to the signal amplifier; and the signal amplifier is configured to amplify the electrical signal and filter out the invalid noise signal from the electrical signal, to obtain the valid electrical signal.

4. The intelligent light adjusting system according to claim 3, wherein the test light sources comprise light sources providing measuring radiation, actinic radiation, saturation radiation, and far-red radiation respectively, and a long wavelength cut-off filter is arranged between the light source providing measuring radiation and the reflective cup.

5. The intelligent light adjusting system according to claim 3, wherein the reflective cup is arranged above leaves for testing of the crops, and a short wavelength cut-off filter is arranged between the leaves for testing of the crops and the photoelectric detector.

6. The intelligent light adjusting system according to claim 1, wherein the light source control device comprises:
- a micro control unit configured to receive the light source parameter outputted by the parameter processing device, and control a pulse width modulation unit based on the light source parameter; and
- the pulse width modulation unit configured to output a current to adjust luminance of the light source assembly, based on the control of the micro control unit.

7. The intelligent light adjusting system according to claim 6, wherein the light source assembly comprises a plurality of light emitting diodes (LEDs), the light source control device further comprises an LED driver circuit, and the pulse width modulation unit is configured to adjust the luminance of the light source assembly by means of the LED driver circuit.

8. The intelligent light adjusting system according to claim 1, wherein,
- the parameter measurement device is configured to transmit the specified parameter to the parameter processing device, in a case that the specified parameter measured currently is greater than a first preset threshold; and
- the parameter measurement device is configured to transmit the specified parameter to the parameter processing device, in a case that the specified parameter measured currently is less than a second preset threshold, wherein the first preset threshold is greater than the second preset threshold.

9. The intelligent light adjusting system according to claim 1, wherein
- the parameter processing device is configured to output a first light source parameter to reduce luminance of the light source assembly, in a case that the specified parameter measured currently is greater than a third preset threshold; or
- the parameter processing device is configured to output a second light source parameter to increase the luminance of the light source assembly, in a case that the specified parameter measured currently is less than a fourth preset threshold, wherein the third preset threshold is greater than the fourth preset threshold.

10. The intelligent light adjusting system according to claim 1, wherein the light source assembly comprises a plurality of light emitting diodes (LEDs).

11. An intelligent light adjusting method in a crop growth process, comprising:
- measuring a specified parameter in the crop growth process; and
- adjusting, based on the specified parameter, a light source parameter of a light source assembly to adjust light for crops,
- wherein the measuring a specified parameter in the crop growth process further comprises:
- sensing, by a photosensitive element, light, converting the sensed light into a valid optical signal and transmitting the valid optical signal to a sensor element;
- converting, by the sensor element, the valid optical signal into an electrical signal and transmitting the electrical signal to a signal conditioning and converting circuit;
- amplifying, by the signal conditioning and converting circuit, a valid signal in the electrical signal and filtering out an invalid noise signal from the electrical signal to obtain a valid electrical signal and transmitting the valid electrical signal to a parameter processing device; and
- comparing, by the parameter processing device, an output of the sensor element and an output of the signal conditioning and converting circuit and give feedback,
- wherein the valid optical signal corresponds to the specified parameter.

12. The intelligent light adjusting method according to claim 11, wherein
- luminance of the light source assembly is reduced, in a case that the specified parameter measured currently is greater than a third preset threshold; or
- the luminance of the light source assembly is increased, in a case that the specified parameter measured currently is less than a fourth preset threshold, wherein the third preset threshold is greater than the fourth preset threshold.

* * * * *